(12) United States Patent
Hattori et al.

(10) Patent No.: US 7,763,723 B2
(45) Date of Patent: *Jul. 27, 2010

(54) **POLYSACCHARIDE AND COMPOSITION FROM *ANTRODIA CAMPHORATA* AND USE THEREOF**

(75) Inventors: Masao Hattori, Toyama (JP); Chia-Chin Sheu, Kuei Shan Hsiang (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 883 days.

This patent is subject to a terminal disclaimer.

(21) Appl. No.: 11/203,410

(22) Filed: Aug. 15, 2005

(65) Prior Publication Data

US 2006/0052337 A1    Mar. 9, 2006

(30) Foreign Application Priority Data

Aug. 17, 2004   (EP)   .................... 04254939

(51) Int. Cl.
C07H 3/08    (2006.01)
C07H 1/08    (2006.01)
A61K 31/715  (2006.01)

(52) U.S. Cl. ............... 536/123.1; 536/127; 514/54
(58) Field of Classification Search ............. 536/123.1, 536/127; 514/54
See application file for complete search history.

(56) References Cited

U.S. PATENT DOCUMENTS

| 6,558,943 | B1 * | 5/2003 | Li et al. | 435/254.1 |
| 6,740,517 | B2 * | 5/2004 | Lan et al. | 435/254.3 |
| 2003/0148517 | A1 * | 8/2003 | Chen et al. | 435/383 |

OTHER PUBLICATIONS

Han et al. Chem. Pharm. Bull., 2006, 54(4), p. 496-500.*
Cheng, Jing-Jy et al., Study for anti-angiogenic activities of polysaccharides isolated from *Antrodia cinnamomea* in endothelial cells, (2005) Life Sciences vol. 75, pp. 3029-3042, 2005.
Lee, I.-Hung, et al., *Antrtodia camphorate* polysaccharides exhibit anti-hepatitis B virus effects, (2002), FEMS Microbiology Letters, vol. 209, pp. 63-67.
Liu, Jun-Jen, et al., Antitumor effects of the partially purified polysaccharides from *Antrodia camphorate* and the mechanism of its action, (2004), Toxicology and Applied Pharmacology, vol. 201, pp. 186-193.
Shen, Yuh-Chiang, et al., Anti-inflammatory activity of the extracts from mycelia of *Antrodia camphorate* cultured with water-soluble fractions from five different *Cinnamomum* species, (2004), FEMS Microbiology Letters, vol. 231, pp. 137-143.

* cited by examiner

*Primary Examiner*—Shaojia Anna Jiang
*Assistant Examiner*—Jonathan S Lau
(74) *Attorney, Agent, or Firm*—WPAT, P.C.; Anthony King; Kay Yang

(57) ABSTRACT

The invention relates to polysaccharide extracted from *Antrodia camphorata* and the method for preparing the polysaccharide. The invention also relates to compositions and methods for hepatoprotective effect.

16 Claims, 16 Drawing Sheets

POLYSACCHARIDE AND COMPOSITION FROM ANTRODIA CAMPHORATA AND USE THEREOF

FIELD OF THE INVENTION

The invention relates to polysaccharide extracted from *Antrodia camphorata* and the method to prepare it. The invention also relates to composition for hepatoprotective effect.

DESCRIPTION OF PRIOR ART

*Antrodia camphorata* (Chinese name, niu-chang-chih or niu-chang-ku) is a new species of the genus *Antrodia* (family poly-poraceae, Aphyllophorales) that is parasitic on the inner cavity of the endemic species *cinnamomum Kanehirai Hey*. It is endangered species in Taiwan. The fruit body of *Antrodia camphorata* is perennial and has a strong smell. It differs a lot from general reishi mushroom in its plate-shaped or bell-shaped appearance. The plate-shaped one is orange red (yellow) with ostioles all over its surface and has light yellow white phellem in bottom layer. It grows by adhering phellem to the inner wall inside a hollow *Antrodia camphorata*. The bell-shaped one also shows orange (yellow) color in fruit body layer (bell surface) that is completely filled with ostioles inside, which are, spores of bitter taste in orange red for fresh state and in orange brown or brown afterward. Bell body is a shell that appears in dark green brown color. The spores look smooth and transparent in slightly curved column shape under the investigation by microscope.

*Antrodia camphorata* is traditionally used for treatment of toxication caused by food, alcohol or drugs, as well as diarrhea, abdominal pain, hypertension, skin itching and cancer (Shen et al., 2004, FEMS Microbiol. Lett., 231: 137-143). In the past, phytochemical investigations have resulted in the isolation of a series of new steroid acids, triterpene acids and polysaccharides (Lieu et al., 2004, Toxicol. Appl. Pharmacol. 201:186-193).

Polysaccharides are common structural and storage polymers in living organisms, representing more than 75% of the dry weight of plants. Compositional analysis of glycoconjugates is important in structural studies of these compounds. Polysaccharides are potentially useful, biologically active ingredients for pharmaceutical uses due to a variety of biological activities, such as mitogenic activity, activation of alternative-pathway complement (APCs) and plasma-clotting activity (Lee et al., 2002, FEMS Microbiol. Lett., 209: 63-67; Chen et al., 2005, Life Sciences, 76: 3029-3042).

The effects of the polysaccharides extracted from *Antrodia camphorata* are anti-hepatitis B virus effects, anti-inflammatory activity, anti-angiogenic activities and antitumor effects (Lee et al., 2002, FEMS Microbiol. Lett., 209:63-67; Shen et al., 2004, FEMS Microbiol. Lett., 231: 137-143; Chen et al., 2005, Life Sciences, 76: 3029-3042; Lieu et al., 2004, Toxicol. Appl. Pharmacol. 201:186-193). However, the component, structure or other characteristics of the polysaccharides extracted from *Antrodia camphorata* are not yet clear identified.

Hepatitis is a common disease in the world especially in developing countries. However, there are no effective drugs for the treatment of this disease. In recent years, scientists have carried out a considerable amount of research on traditional medicine in an attempt to develop new drugs for hepatitis. Compounds that can either decrease the necrotic damage to hepatocytes via enhanced defense mechanisms against toxic insult or improve the repair of damaged hepatocyte are considered potentially useful in the treatment of human hepatitis.

BRIEF DESCRIPTION OF THE DRAWINGS

FIG. 8 illustrates GC-MS analysis of sugar composition of ACN2a.

FIG. 9 illustrates determination of the absolute configurations (D/L) of the component sugars of the ACN2a.

SUMMARY OF THE INVENTION

Figure 4:
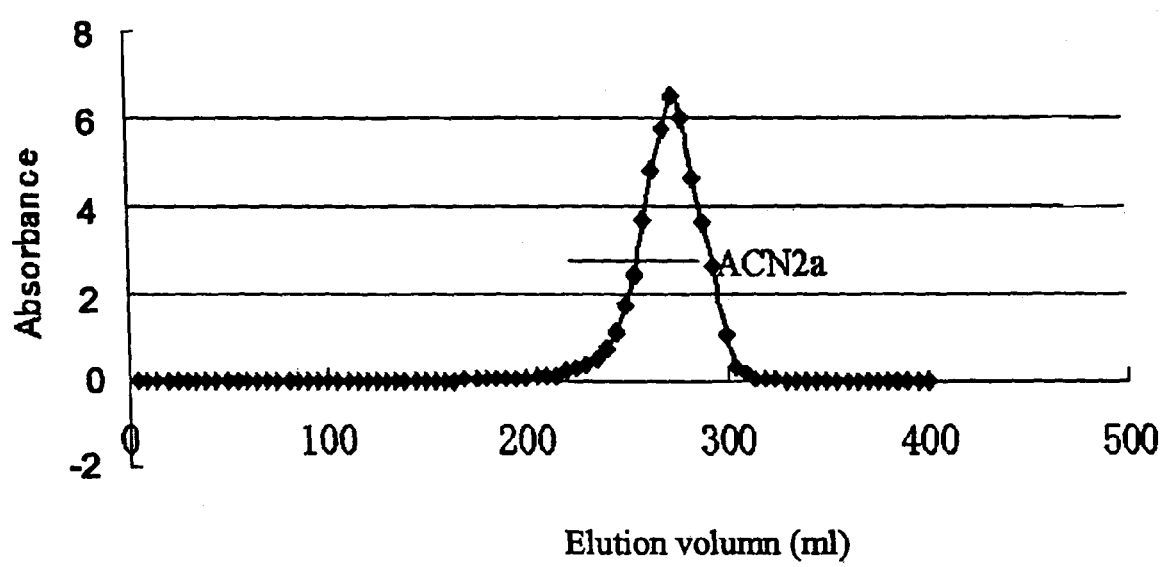
FIG. 4 illustrates elution profile of ACN2-1 by gel filtration column chromatography on HW-65 (Detection was performed by phenol-$H_2SO_4$ method).
Figure 5:
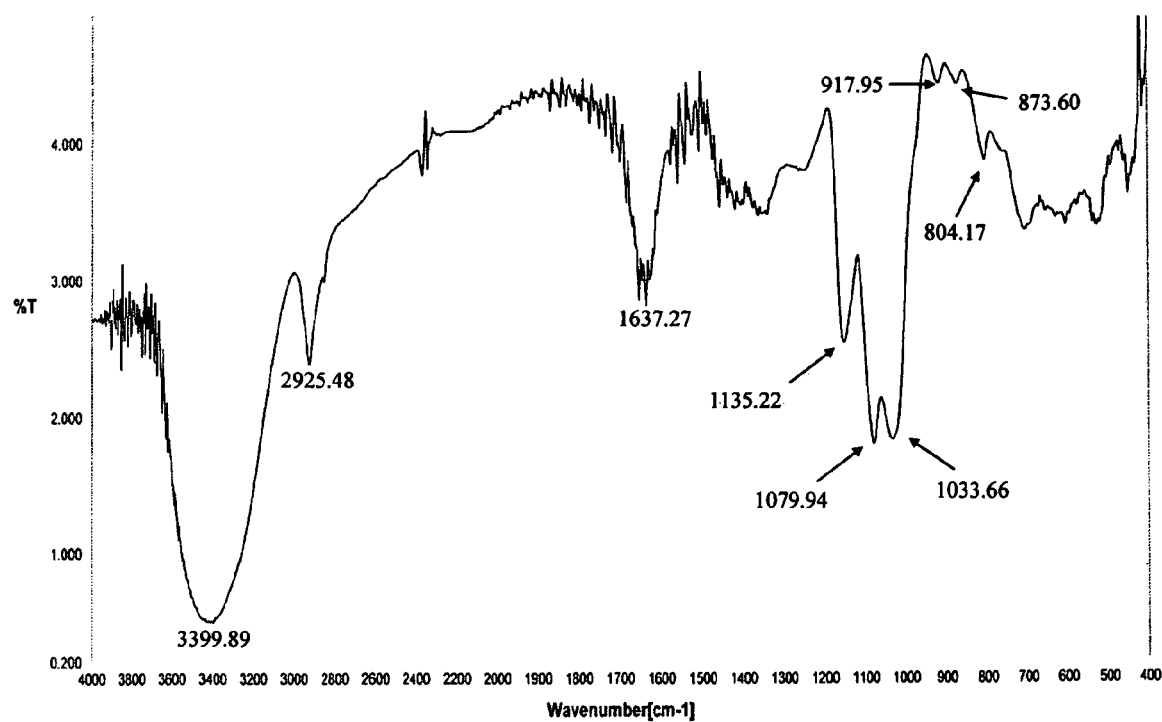
FIG. 5 illustrates IR spectrum of ACN2a (measured with KBr method).
Figure 6:
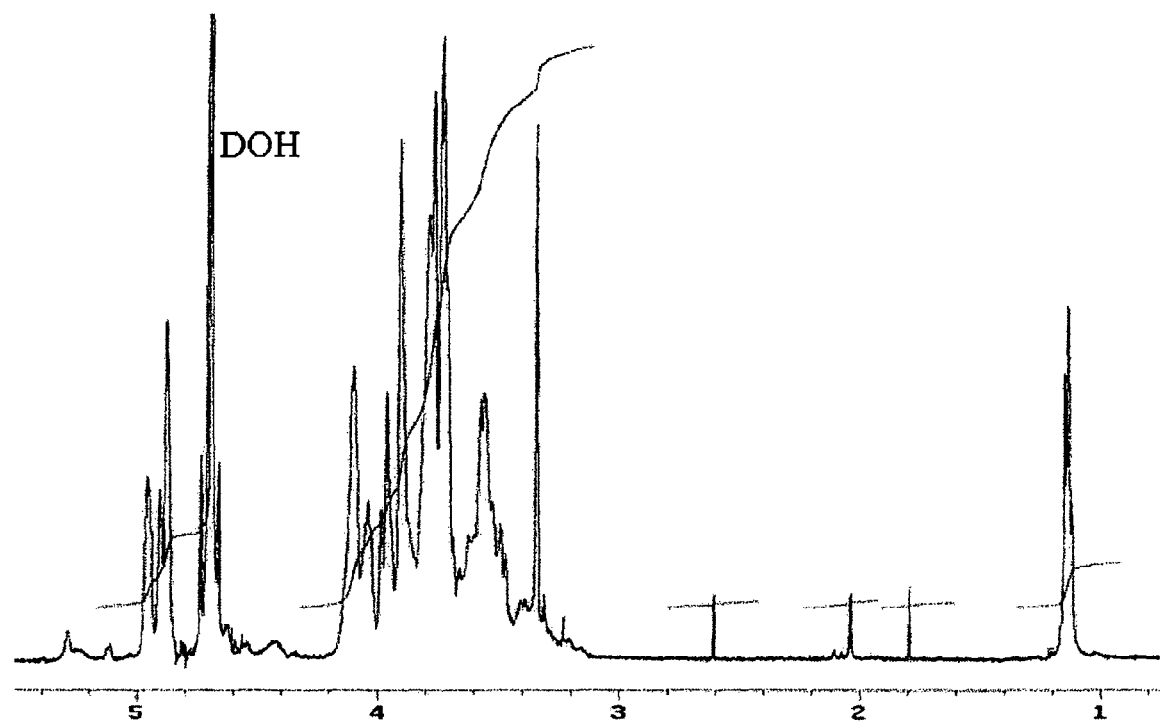
FIG. 6 illustrates $^1$H-NMR spectrum of ACN2a (measured in $D_2O$).
Figure 7:
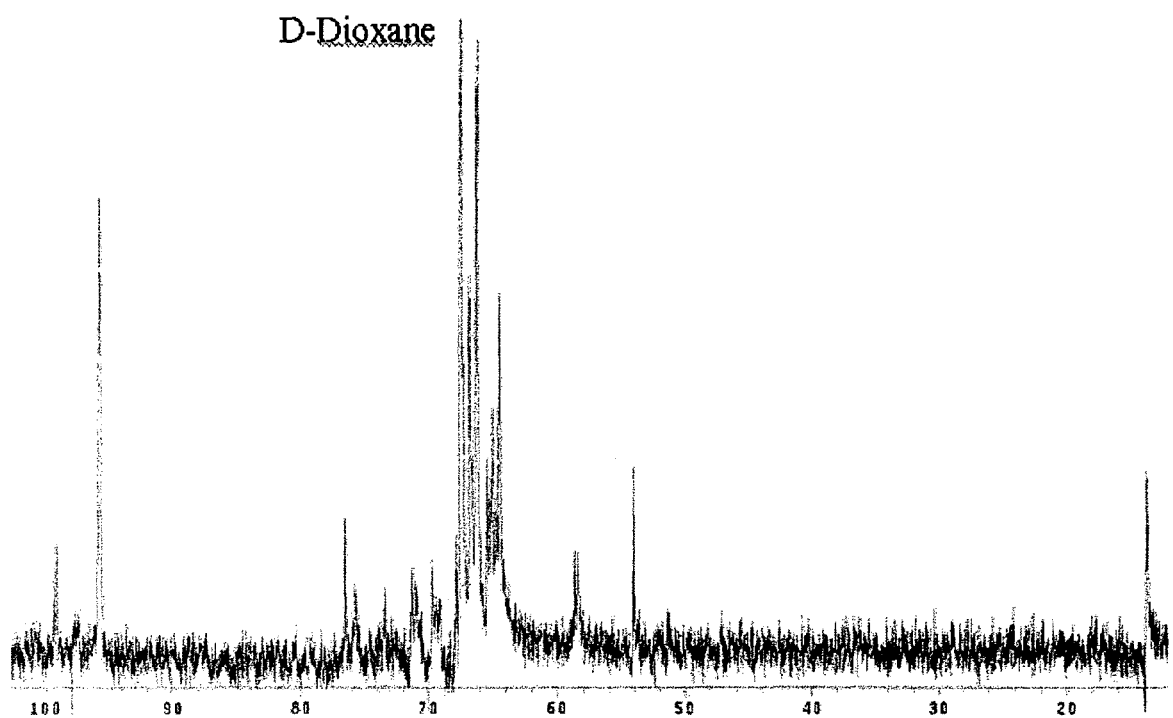
FIG. 7 illustrates $^{13}$C-NMR spectrum of ACN2a (measured in $D_2O$).
Figure 8:
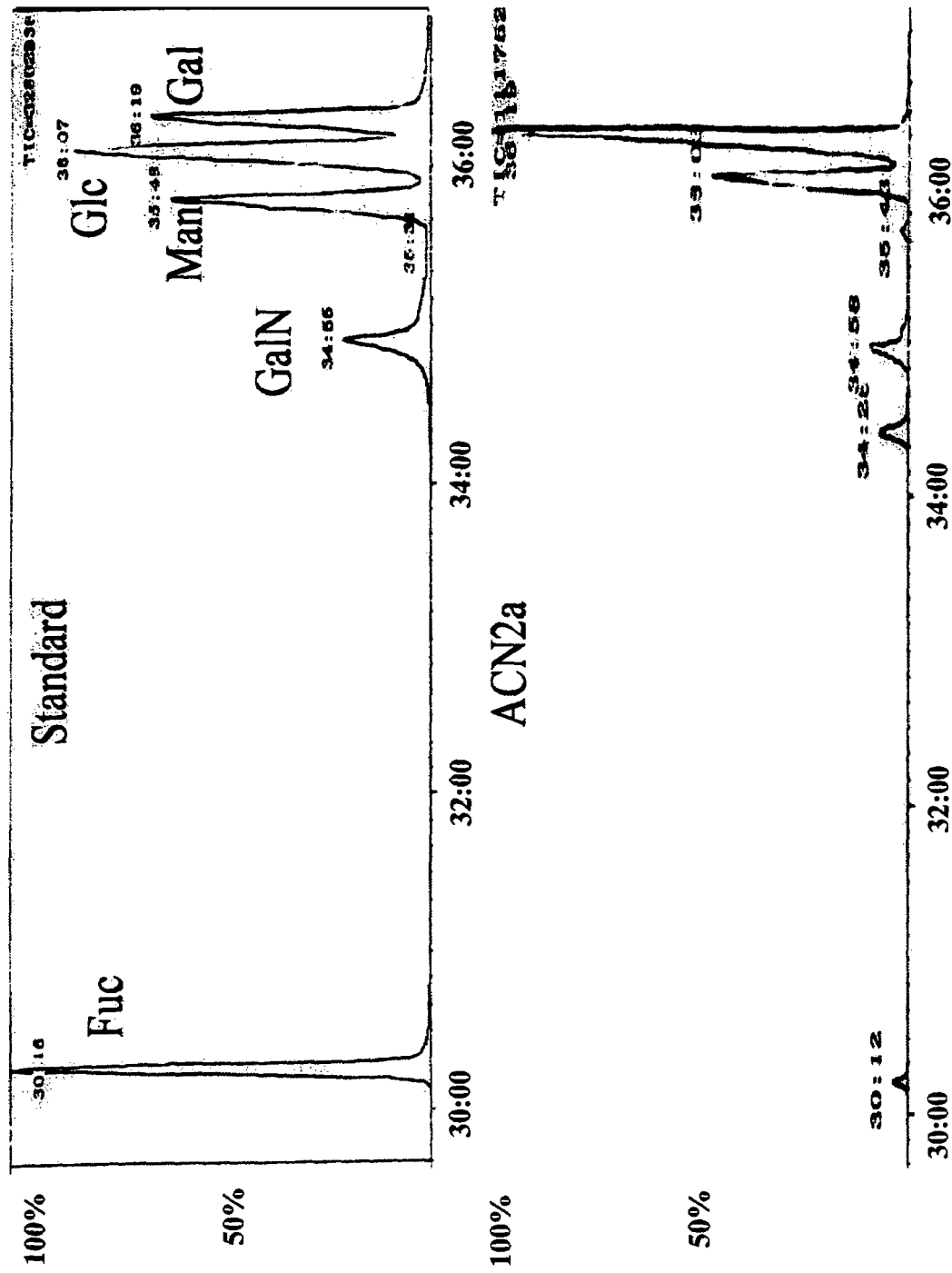
Figure 9:
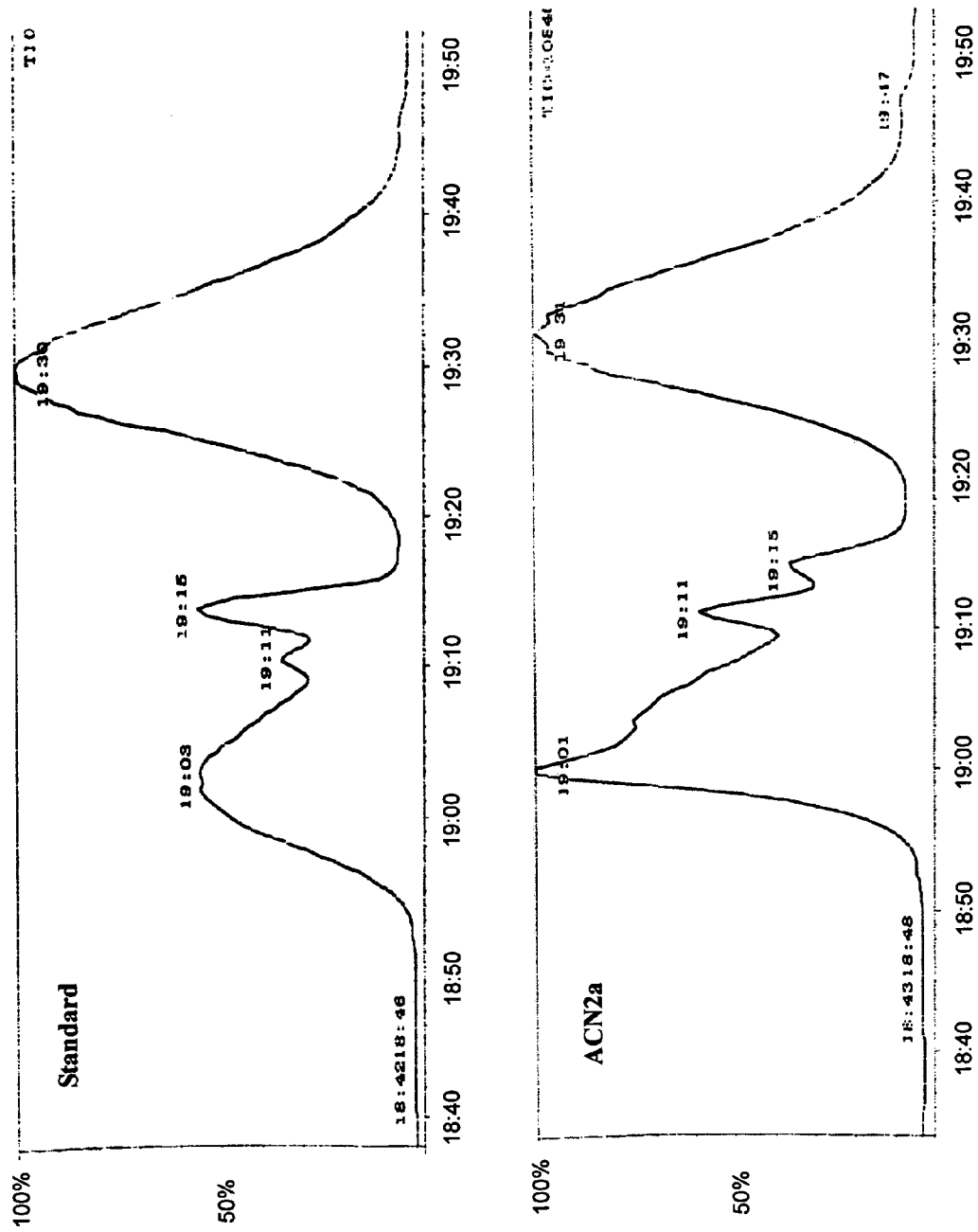

The invention provides a polysaccharide extracted from *Antrodia camphorata* having characteristics as follows: (a) appearance: colorless and shapeless powder, (b) pH: neutral, (c) molecular weight: 1285 kDa determined by HPLC as shown in FIG. 4, (d) rotatory power: $[\alpha]_D$+115.0° (c=0.4433, $H_2O$), (e) intrinsic viscosity: $[\eta]$=0.0417 dl·g$^{-1}$, (f) specific heat Cp: 0.2663 Cal/g·°C., (g) IR spectrum: as shown in FIG. 5, (h) $^1$H-NMR spectrum: as shown in FIG. 6, (i) $^{13}$C-NMR spectrum: as shown in FIG. 7, and (j) GC-MS analysis: as shown in FIG. 8.

The invention also provides a method for extracting polysaccharide from *Antrodia camphorata* comprising: (a) extracting the *Antrodia camphorata* by water, (b) collecting the precipitates of the mixture, and (c) dialyzing the TCA-soluble fraction.

The invention further provides a composition for hepatoprotective effects comprises water extract from *Antrodia camphorata*.

This invention further provides a method for providing hepatoprotective effect comprises administering a patient with an effective amount of water extract from *Antrodia camphorata*.

DETAILED DESCRIPTION OF THE INVENTION

This invention provides a polysaccharide extracted from *Antrodia camphorata* having characteristics as follows: (a) appearance: colorless and shapeless powder, (b) pH: neutral, (c) molecular weight: 1285 kDa determined by HPLC as shown in FIG. 4, (d) rotatory power: $[a]_D$+115.0° (c=0.4433, $H_2O$), (e) intrinsic viscosity: $[\eta]$=0.0417 dl·g$^{-1}$, (f) specific heat Cp: 0.2663 Cal/g·°C., (g) IR spectrum: as shown in FIG. 5, (h) $^1$H-NMR spectrum: as shown in FIG. 6, (i) $^{13}$C-NMR spectrum: as shown in FIG. 7, and (j) GC-MS analysis: as shown in FIG. 8. The IR spectrum of the polysaccharide shows the component sugars comprising galactose, glucose, fucose, mannose and galatosamine. The $^1$H-NMR spectrum of the polysaccharide shows the component sugars comprising D-galactose, D-glucose, L-fucose and D-mannose. The ratio of the component sugars comprising galactose, glucose, fucose, mannose and galatosamine is 1:0.24:0.07:0.026:faint. The component sugars have main chain consisting of: (a) terminal residue: fucose or glucose, and (b) middle residue: 1,3-linked glucose, 1,4-linked glucose, 1,6-linked and 1,2,6-linked galactose, wherein the 1,2,6-linked galactose residue is attached by the branch chain at 2-O site. The polysaccharide of this invention has galactose in main backbone and can be linear or branch form.

The polysaccharide of this invention is extracted from *Antrodia camphorata* by water. The extraction is from mycelium or fruit body of *Antrodia camphorata*.

This invention also provides a method for extracting polysaccharide from *Antrodia camphorata* comprising: (a) extracting the *Antrodia camphorata* by water, (b) collecting the precipitates of the mixture, and (c) dialyzing the TCA-soluble fraction. The step (a) is at around 60-120° C. and the step (b) is left the mixture at around 0-20° C. The precipitates of step (b) are treated with trichloroacetic acid (TCA).

The invention provides a composition for hepatoprotective effects comprises water extract from *Antrodia camphorata*. In a preferred embodiment of the invention, the water extract comprises the polysaccharide of the invention.

The term "hepatoprotective effect" used in the invention is not limited but to prevent or reduce the hepatocyte necrosis (such as prevention or reducing via scavenging oxygen free radical formation, increasing IL-2, or decreasing cytotoxic T lymphocyte) or against fulminant hepatitis.

The composition further comprises a pharmaceutical carrier, buffer, diluent, or excipient. The suitable diluents are polar solvents, such as water, alcohol, ketones, esters and mixtures of the above solvents, preferably water, alcohol and water/alcohol mixture. For the preferable embodiment, the suitable solvents are water, normal saline, buffering aqueous solution and buffering saline etc. The excipients used with the composition of this invention can be in liquid, semi-liquid or solid form, such as lactose, dextrin, and starch and sodium stearate. Liquid excipients include water, soybean oil, wine and juices etc.

The compositions can be administered by oral or injection. The compositions can be taken by oral in liquid, semi-liquid or solid form. The compositions provided by injection are in liquid or semi-liquid form. The injection includes intravenous injection, the abdominal cavity and intramuscular injection.

The present invention also provides a method for providing hepatoprotective effect comprises administering a patient with an effective amount of water extract from *Antrodia camphorata*. In a preferred embodiment of the method, the water extract is the polysaccharide of the invention. The administration route is via oral or injection. The polysaccharide can be administered with pharmaceutical carrier, buffer, diluent, or excipient, in liquid, semi-liquid or solid form. The suitable diluents are polar solvents, such as water, alcohol, ketones, esters and mixtures of the above solvents, preferably water, alcohol and water/alcohol mixture. For the preferable embodiment, the suitable solvents are water, normal saline, buffering aqueous solution and buffering saline etc. The excipients used with the composition of this invention can be in liquid or solid form, such as lactose, dextrin, and starch and sodium stearate. Liquid excipients include water, soybean oil, wine and juices etc. The polysaccharide can be taken by oral in liquid, semi-liquid or solid form. The polysaccharide provided by injection is in liquid or semi-liquid form. The injection includes intravenous injection, the abdominal cavity and intramuscular injection.

EXAMPLE

The following examples serve to exemplify the present invention but do not intend to limit the scope of the present invention Example 1

(A) Materials

*Antrodia camphorata* mycelium was provided by Simpson Biotech Co. Ltd. (Taiwan). A standard molecular weight market of pullulans (Shodex Standard P-82) was purchased from Showa Denko Co. Ltd., (Japan).

(B) General Experimental Procedures

Optical rotation was determined in $H_2O$ with a JASCO DIP-360 automatic polarmater. UV absorptions were measured with a SHIMADZU UV-2200 UV-VIS recording spectrometer. IR spectra were recorded in a KBr disk or liquid film using a JASCO FT/IR-230 infrared spectrometer. NMR spectra were recorded on Varian Unity Plus 500 (H was at 500 MHz, C was at 125 MHz) and Varian GEMINI 300 (H was at 300 MHz, C was at 75 MHz). A solution of polysaccharide in $D_2O$ was measured with 1,4-diozane as an external reference. GC-MS analysis was carried out on a SHIMADZU GC-17A gas chromatography equipped with JEOL mass Spectrometer. TLC was carried out on pre-coated silica-gel 60 F254 plates (Merck, 0.25 mm), cellulose F plates (Merck, 0.1 mm), and spots were detected by spraying with 10% H2SO4 or AHP by heating at 100° C. Carbohydrates were determined by the phenol-H2SO4 method.

Example 2

Preparation of Neutral Polysaccharide from *Antrodia Camphorata*

(A) Extraction and Fractionation of Polysaccharides

The freeze-dried power of *Antrodia Camphorata* (1.5 kg) was extracted with $CHCl_3$ (41×3 times) at room temperature for 1 day, then filtered and dried. The residue was dipped into $H_2O$ at room temperature for 1 h and extracted (3 times) at 100° C. for 2 h. After the hot water extract were combined and concentrated to 800 ml, and 3200 ml of EtOH was added to the extract. The mixture was stirred and left in the refrigerator for one night. The precipitate was filtered and washed with cold EtOH, then dried. After treatment of the precipitate with 10% trichloroacetic acid (TCA), the TCA-soluble fraction obtained by centrifugation (3000 rpm×10 min) was extensively dialyzed for 3 d against distilled water. The nondialyzed portion was lyophilized to give a brownish residue (AC). Yield: 14.25 g.

(B) Ion-Exchange Column Chromatography of AC

AC (100 mg) dissolved in $H_2O$ was applied to a column of DE-52 (Whatman international Ltd. England. 2.0×20 cm) The column was eluted with 60 ml of $H_2O$, 60 ml of 0.5M NaCl, 60 ml of 1M NaCl, 60 ml of 2M NaCl, and fractions of every 2 ml were collected. $H_2O$ fraction (ACN) was concentrated and lyophilized to yield 68.3 mg.

(C) Gel Filtration of ACN

ACN (68.3 mg) was dissolved in 0.2M NaCl solution and applied to a column of Toyopearl HW-65 (Tosoh, Tokyo, Japan. 2.0×90 cm). The column was eluted with the same solution, and fractions of every 5 ml were collected. The eluted fractions were separated into two fractions (ACN1 and ACN2) according to the elution profile prepared on the basis of the phenol-$H_2SO_4$ method at 480 nm. Yield: ACN1, 19 mg; ACN2, 49 mg. ACN2 was further purified by the column of HW-65 at the same condition as described above. A colorless polysaccharide was got (named ACN2a, yield: 41 mg).

Figure 1:
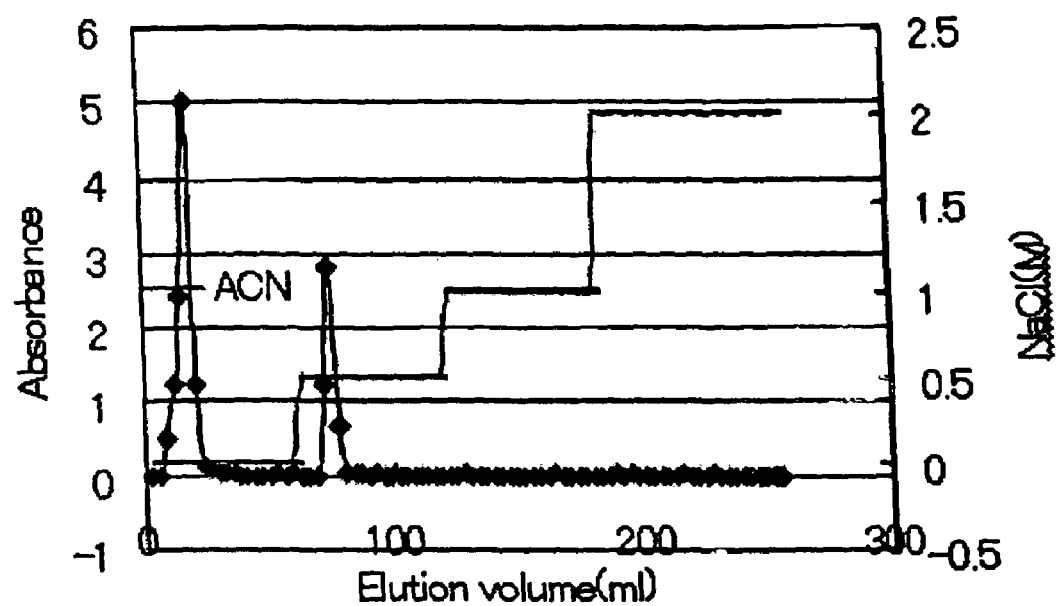
FIG. 1 illustrates elution profile of *Antrodia camphorata* (ACN) by ion exchange column chromatography on DE-52 (Detection was performed by phenol-$H_2SO_4$ method).
Figure 2:
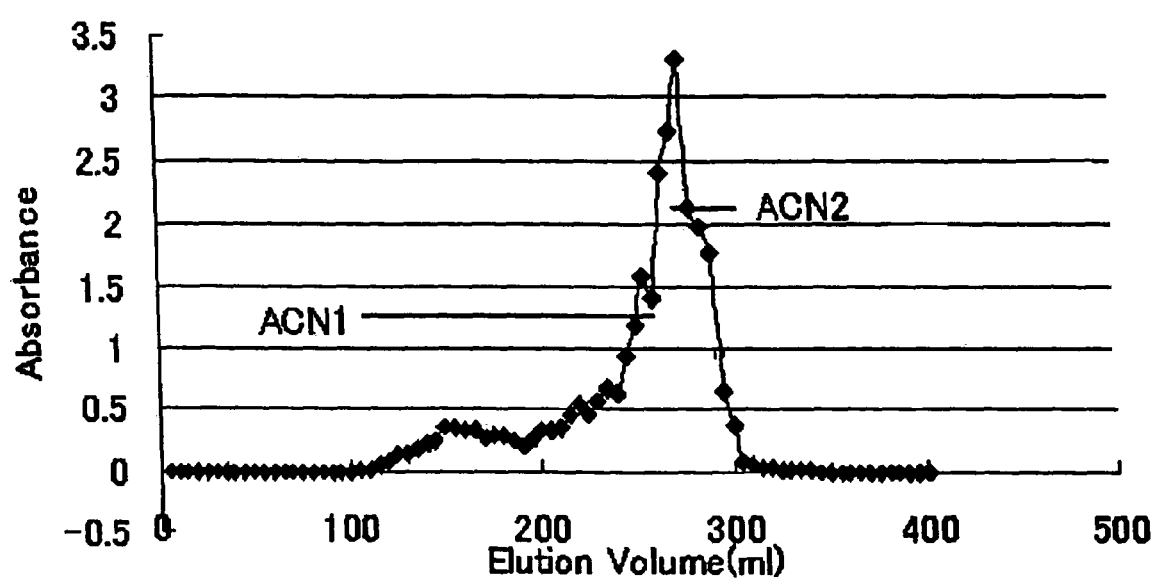
FIG. 2 illustrates elution profile of ACN by gel filtration column chromatography on HW-65 (Detection was performed by phenol-$H_2SO_4$ method).
Figure 3:
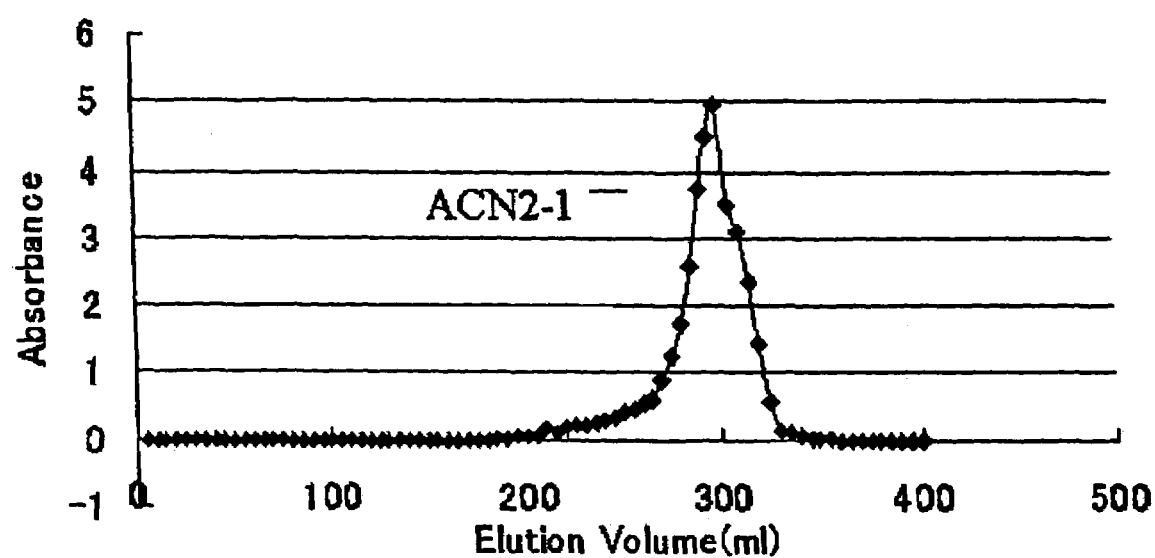
FIG. 3 illustrates elution profile of ACN2 by gel filtration column chromatography on HW-65 (Detection was performed by phenol-$H_2SO_4$ method).

The hot water extract of the *Antrodia camphorata* was fractionated as shown in chart 1. The non-dialyzable portion (AC) of the 10% TCA soluble fraction had hepatoprotective active and contained polysaccharide because the phenol-$H_2SO_4$ reaction was positive. As shown in FIG. 1, AC was separated by ion-exchange column chromatography on DE-52 cellulose. The most potent water fraction (CAN) was then separated by gel filtration (FIG. 2). The second fraction ACN2a was further purified by gel filtration on HW-65 to yield a colorless polysaccharide (ACN2a) as hepato-protective component (FIG. 3).

Example 3

The Structure Analysis of Neutral Polysaccharide from *Antrodia Camphorata*

(A) Estimation of Molecular Weight

The average molecular weight of the polysaccharide (ACN2a) was estimated by HPLC analysis. The sample was applied on a TSK-GMPWXL gel filtration column (7.8×300 mm i.d., Tosoh Corp., Tokyo, Japan) and eluted with 0.2M NaCl at 1 ml/min. Commercial available pullulans (Shodex Standard P-82) were used as standard molecular markers.

This polysaccharide (ACN2a) was proved a single fraction by HPLC (FIG. 4), and its apparent molecular weight was estimated to be 1285320 by HPLC. The polysaccharide is colorless and shapeless powder, and has $[\alpha]$ D+115.0° (c=0.4433, $H_2O$); Intrinsic viscosity $[\eta]$=0.0417 dl $g^{-1}$ (measured with Ostwald viscometer), and Specific heat Cp: 0.2663 Cal/g° C. (measured by DSC method (differential scanning calorimeter). There are 0.20% protein (measured by Bradford method) and 0.12% nitrogen (by elementary analysis method) in the ACN2a; Sulfate is not present in the ACN2a (measured by Barium rhodizonate method).

(B) Identification of Component Sugars

The polysaccharide (2 mg) was dissolved in 2 ml of 2N trifluoroacetic acid (TFA) and sealed. After being hydrolyzed for 1 h at 125° C. in a steam autoclave, TFA was removed by evaporation of the reaction mixture to dryness. The hydrolysates were reduced with $NaBH_4$. Trimethyl-silylation was prepared with silblender-HTP for GC-MS analysis. (Column, DB-1, J&W Scientific, 0.25 mm i.d.×30 m; column temperature, 50° C.~190° C., 5° C./min; then 190° C., 12 min; Helium carrier flow 4.25 kgf/cm).

According to identification of component sugars (FIG. 5), the polysaccharide consisted of galactose, glucose, fucose, mannose and galatosamine (1:0.24:0.07:0.026:faint). About 62.38% sugar of component sugar is galactose. The rotatory power of ACN2a is +115.0° (c=0.4433, $H_2O$). This result suggests that component sugars had a-D- or β-L-configuration possibly (by the isorotation law of Hudson). According to determination of the absolute configuration of component sugars (FIG. 6), the absolute configuration of component sugars was L-fucose, D-galactose, D-glucose and D-mannose respectively.

(C) Determination of the Absolute Configuration of Component Sugars

Determination of the absolute configuration of component sugars was performed as reported by Hara et al. polysaccharide (1 mg) was hydrolyzed in 2N trifluoroacetic acid (TFA) at 125° C. for 1 h. TFA was removed by evaporation to give a sugar fraction. Pyridine solutions (0.5 ml) of the sugar fraction (2 mg) and L-cysteine methyl ester hydrochloride (3 mg) were mixed, and warmed at 60° C. for 1.5 h, then dried with N2. The dried sample was trimethylsilylated with silblender-HTP (0.4 ml) at 60° C. for 1 h. After partitioning with $CHCl_3$ (3 ml) and $H_2O$ (3 ml), the $CHCl_3$ extract was analyzed by GC-MS (Column, DB-wax, J&W Scientific, 30 m×0.25 mm; column temperature, 50° C.~230° C., 10° C./min; then 230° C., 12 min; Helium carrier flow 4.25 kgf/cm)

(D) Methylation Analysis

The polysaccharide (5 mg) was methylated with methyl iodide by Anumula and Taylor's method. Methylated polysaccharides were hydrolyzed with 4N trifluoroacetic acid (TFA) for 90 min at 125° C. in a steam autoclave. After TFA was removed by evaporation, the hydrolysates were converted to alditols with 1M $NH_4OH$ containing 3 mg/ml $NaBH_4$ then acetylated. The partially methylated alditol acetates were analyzed by GC and GC-MS (Column, Sp-2330, Supelco, Bellefnte, Pa., 60 m×0.25 mm, 0.20 um film thickness. Helium was used as a carrier gas, and column temperature was 160° C. to 210° C. at 2° C./min, then 210° C. to 240° C. at 5° C./min and 240° C., 14 min). Peak areas were corrected using published molar response factors. The derivatized compounds were identified by comparison of their relative retention time to 1,5-di-O-acetyl-2,3,4,6-tetra-O-methylglucitol and their GC-EI-MS fragmentation patterns.

In the FT-IR spectrum, as shown in the FIG. 6, pyranoid form was suggested to be present because of the obserbation of three absorption bands at 1153.22 $cm^{-1}$, 1079.94 $cm^{-1}$ and 1033.66 $cm^{-1}$ (Furanose form has only two absorption bands in the region). D-Glucopyranose was suggested to be present because of the absorption band at 917.95 $cm^{-1}$. In addition, the band at 873.6 $cm^{-1}$ is a special absorption band of mannopyranoid and galactopyranoid. Aminosugar was suggested to be present because of the observation of a —NH2 absorption band at 1637.27 $cm^{-1}$. It is the same as analysis conclusion of elementary analysis.

In the HNMR spectrum (FIG. 7), $H^{-1}$ signals were observed at more than 4.8 ppm (4.885, 4.909, 4.963 ppm), which suggest that component sugars have α-configuration. It is the same as analysis conclusion of rotatory power. In addition, at less than 4.8 ppm (4.738, 4.663 ppm), $H^{-1}$ signals were also observed. This results suggest that component sugars have also little β-configuration. Methyl proton signal was observed at 1.134 ppm, which was assigned to the methyl of fucose residues. Anomeric signal was detected at less than 5.0 ppm as singlet. These results suggest that fucose residue have a β-L-configuration. (Anomeric signal of α-L-fucose was observed at more than 5.0 ppm).

In the CNMR spectrum (FIG. 8), C-4 and C-5 signals were observed at less than 80 ppm. This result suggests that component sugars are pyranoid form (The chemical shifts of C-4 and C-5 for furanose form are present in the region 80~85 ppm) It is the same as analysis conclusion of IR. In addition, methyl signal was observed at 13.7 ppm, which was assigned to the methyl of fucose residues. This result suggest that fucose residues are L-fucoses (C-6 signal of $_D$-fucose is observed in the region 60~65 ppm). It is the same as analysis conclusion of HNMR spectrum.

The results of methylation analysis, as summarized in Table 1, showed that ACN2a was composed of terminal-Fucose, 1,4-linked glucose, 1-6 linked and 1,2,6-linked galactose residues, and little terminal and 1,3-linked glucose residues, and little terminal and 1,3-linked glucose residues. By the methylation analysis, ACN2a contained a backbone composed of α-D-1,6-Gal (α-D-1,6- and α-D-1,2,6-) Gal, it is about 72.82%. And the number of branch points were about 15.75% of total residues' numbers, the branch was attached to 2-O of a galactosy residues of the main chain.

TABLE 1

The results of methylated analysis of ACN2a

| Methylated sugar | Molar ratio | $T_R$ | MS main fragments (M/Z) | Linkages type |
|---|---|---|---|---|
| 2,3,4-Me$_3$-Fuc | 0.209 | 0.789 | 71, 89, 101, 117, 131, 161, 175 | Fuc-(1→ |
| 2,3,4,6-Me$_4$-Glc | 0.084 | 1 | 71, 87, 101, 117, 129, 145, 161, 205 | Glc-(1→ |
| 2,4,6-Me$_3$-Glc | 0.026 | 1.31 | 71, 87, 101, 117, 129, 161, 233 | →3)-Glc-(1→ |
| 2,3,6-Me$_3$-Glc | 0.157 | 1.489 | 87, 99, 101, 113, 117, 233 | →4)-Glc-(1→ |
| 2,3,4-Me$_3$-Glc | 1 | 1.6 | 71, 87, 99, 101, 117, 129, 161, 189 | →6)-Glc-(1→ |
| 3,4-Me$_3$-Gal | 0.276 | 1.881 | 87, 99, 129, 189 | →2,6)-Glc-(1→ |

$T_R$ is the relation time of each component, relative to that of 1, 5-O-2, 3, 4, 6-Me$_4$-Glc Example 4

Protective Effect of the Neutral Polysaccharide (ACN2a) Against *P. Acnes*-LPS Induced Hepatoxicity (A) Preparation of *P. Acbes* and Reagent

*P. acnes* (ATCC 6919) was cultured with brain heart infusion medium (Wako pure chemical industries, Ltd. Osaka, Japan) supplemented with L-cysteine (0.03%) and Tween 80 (0.03%) under anaerobic conditions for 48 h at 37° C. Cultured cells were centrifuged at 7000 rpm for 15 min at 4° C. and washed with Phosphate-buffered saline (PBS). The bacterial pellet was resuspended with PBS and the cells were killed by heat treatment at 80° C. for 30 min, and then lyophilized to prepare the heat-killed *P. acnes* powder. LPS from *Escherichia coli* 055:B5 was purchased from Sigma-aldrich, Inc. FK506 (tacrolimus hydrate) was provided by Fujisawa Pharmaceutical Co., Ltd. (OSAKA, Japan).

(B) Animals

To study the protective effect against hepatoxicity induced by *P. acnes*-LPS, four-week-old male ICR mice (SLC, Japan) weight 18~20 g were used for the experiment. The animals were acclimatized for one week before the study.

(D) Experiment

The hepatoprotective activity of ACN2a was investigated using: (1) normal control (untreated); (2) *P. acnes*+LPS; ACN2a [(3) 0.2 g/kg, (4) 0.4 g/kg, (5) 0.8 g/kg of body weight (b. w.)] plus *P. acnes*+LPS; and (6) FK506 (1 mg/kg of body weight) plus *P. acnes*+LPS.

Heat-killed *P. acnes* dissolved in saline was injected via a tail vein at a dose of 0.15 mg/mouse. Seven day later, acute liver damage was induced by intravenous injection of LPS at a dose of 0.05 μg/mouse. ACN2a was given once daily by gastric tube to the animals for 7 consecutive days. On the 8$^{th}$ day, after 1 h of ACN2a was given, LPS was injected. FK506 was used as positive control drug and administered by gastric tube 48, 36, 24, 12 and 1 hr before intravenous injection of LPS. Blood samples were taken into tubes for analysis of liver injury 6 h after LPS injection, and these animals were sacrificed. The tubes were centrifuged at 4000 rpm for 15 min and the supernatant was used as a sample. All samples were stored at −20° C. until the assay. The serum ALT and AST activity, which are markers of hepatocyte injury were determined using kits for the measurement of enzyme activity (Wako pure chemical industries, Ltd. Osaka, Japan)

Figure 10:
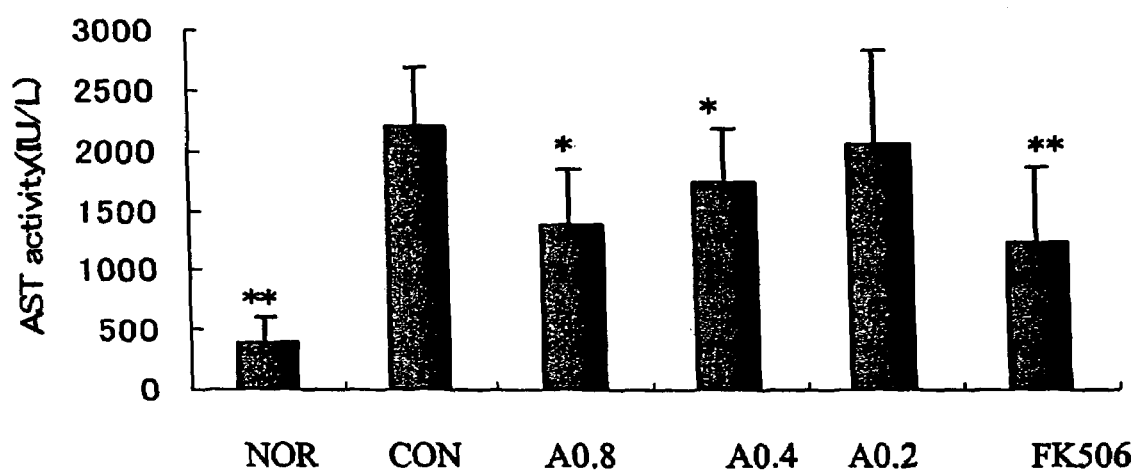
FIG. 10 illustrates the effects of ACN2a on serum AST levels in ICR mice with *P. acnes*-LPS induced liver injury. Nor: normal control; Con: *P. acnes*-LPS; A0.8: ACN2a 0.8 g/kg(b.w.)+*P. acnes*-LPS; A0.4: ACN2a 0.4 g/kg(b.w.)+*P. acnes*-LPS; A0.2: ACN2a 0.2 g/kg(b.w.)+*P. acnes*-LPS; FK506: FK506 1 mg/kg(b.w.)+*P. acnes*-LPS. The results represent the mean±S.D. of the values obtained 10 mice in each group. *: $P<0.05$ and **: $p<0.01$ compare to corresponding *P. acnes*-LPS control group as determined with student's t-test.
Figure 11:
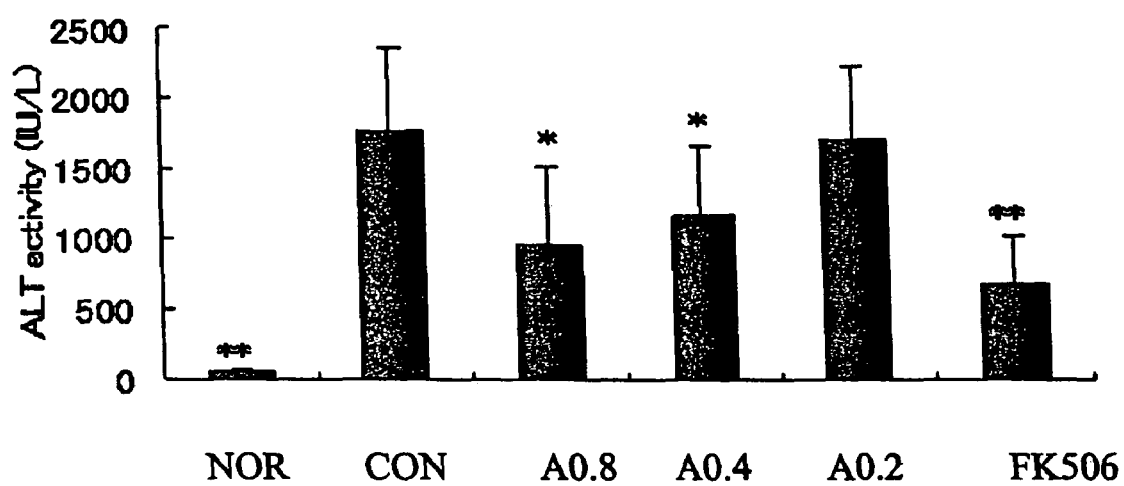
FIG. 11 illustrates the effects of ACN2a on serum ALT levels in ICR mice with *P. acnes*-LPS induced liver injury. Nor: normal control; Con: *P. acnes*-LPS; A0.8: ACN2a 0.8 g/kg(b.w.)+*P. acnes*-LPS; A0.4: ACN2a 0.4 g/kg(b.w.)+*P. acnes*-LPS; A0.2: ACN2a 0.2 g/kg(b.w.)+*P. acnes*-LPS; FK506: FK506 1 mg/kg(b.w.)+*P. acnes*-LPS. The results represent the mean ±S.D. of the values obtained 10 mice in each group. *: $P<0.05$ and **: $p<0.01$ compare to corresponding *P. acnes*-LPS control group as determined with student's t-test.

FIGS. 10 and 11 showed the effect of ACN2a on ALT and AST levels in serum of mice treated with *P. acnes*-LPS. The acute hepatoxicity reaction was significantly (P<0.05) suppressed in all of the animals pretreated with 0.4 and 0.8 g/kg of body weight of ACN2a. So ACN2a had protective effect against *P. acnes*-LPS induced hepatic toxicity in mice; moreover, these protective effect was found to be dose dependent.

Figure 12:
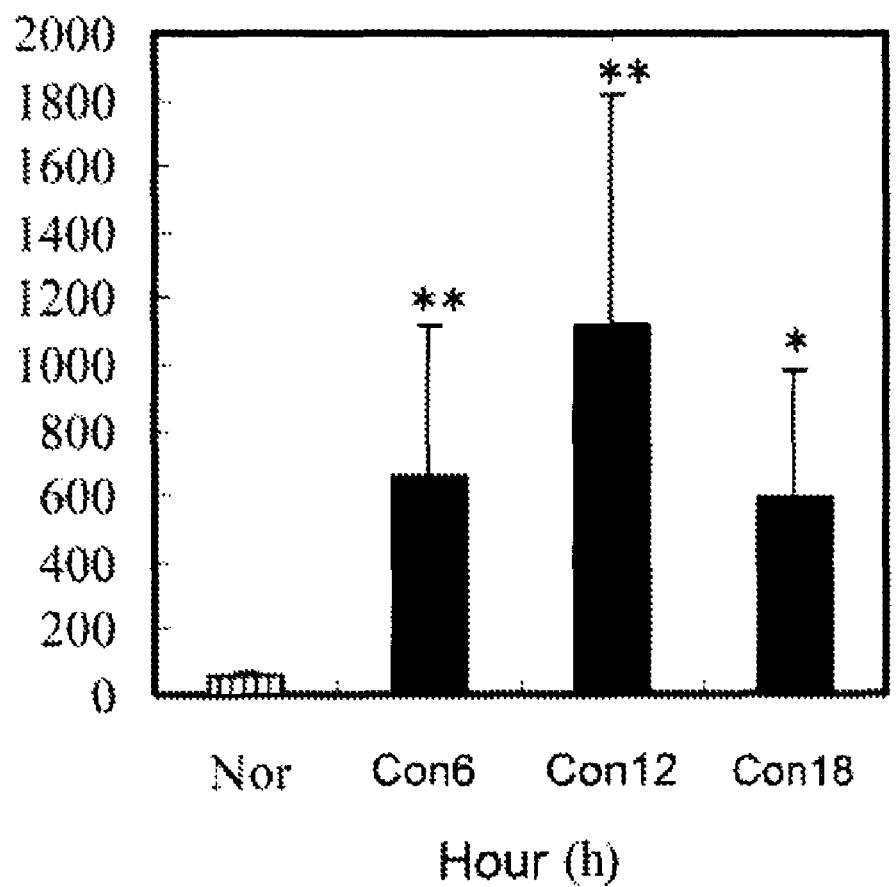
FIG. 12 illustrates serum AST levels dependence of hour. Nor: normal control; Con6: the blood samples are collected 6 hrs after intravenous injection of LPS; Con12: the blood samples are collected 12 hrs after intravenous injection of LPS; Con18: the blood samples are collected 18 hrs after intravenous injection of LPS. The results represent the mean±S.D. of the values obtained 10 mice in each group. *: $P<0.05$ and **: $p<0.01$ compare to corresponding *P. acnes*-LPS control group as determined with student's t-test.
Figure 13:
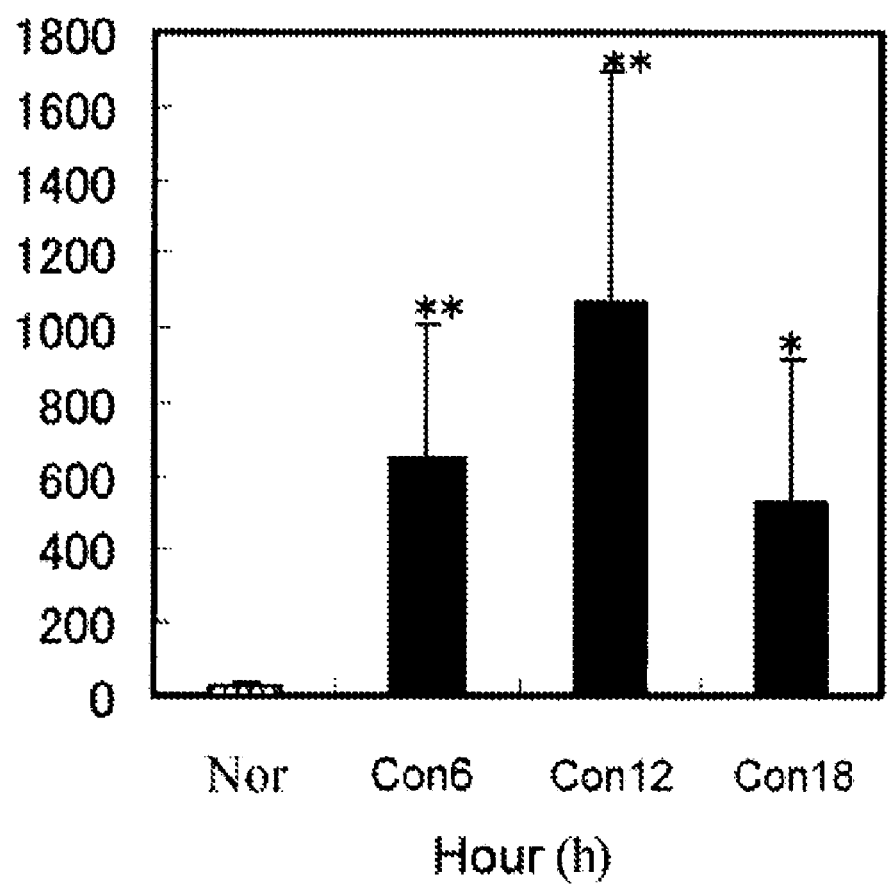
FIG. 13 illustrates serum ALT levels dependence of hour. Nor: normal control; Con6: the blood samples are collected 6 hrs after intravenous injection of LPS; Con12: the blood samples are collected 12 hrs after intravenous injection of LPS; Con18: the blood samples are collected 18 hrs after intravenous injection of LPS. The results represent the mean±S.D. of the values obtained 10 mice in each group. *: $P<0.05$ and **: $p<0.01$ compare to corresponding *P. acnes*-LPS control group as determined with student's t-test.

Injection of *P. acnes* followed by LPS is useful for the creation of experimental models of acute hepatic damage. Most of the animals died from severe liver injury within 24 hr of LPS injection. In this study, we found the best dose of *P. acnes*-LPS (0.15 mg-0.05 ug/mouse). All of animals survived from severe liver injury, and liver injury was the severest 12 hr after intravenous injection of LPS (FIGS. 12 and 13). So in this invention, the blood samples were collected for analysis of liver injury 6 hr after LPS injection.

Example 6

Mechanism of the Hepaprotective Model

Mechanism of the experimental model induced by *P. acnes*-LPS was shown in chart 2. Injection of *P. acnes* into mice via a tail vein results in monocytic infiltration of the liver, so hepatic macrophages were increase, and subsequent intravenous injection of a small amount of LPS activated hepatic macrophage. Cytokines of tumor necrosis factor (TNF) IL-1, soluble IL-2 receptor etc., were gone out of hepatic macrophage and increased. Then liver was injured via three ways by these cytokines: 1). TNF and IL-1 broadly necrosised hepatocyte via platelet activating factor (PAF) and leukotriene etc. 2) TNF and IL-1 broadly necrosised hepatocyte via neutrophi and microcirculation lesion. In this way, oxygen free radicals played a major role. 3) IL-2 was decreased because of combining with soluble IL-2 receptor, results in suppressor T cell decreasing and cytotoxic T cell (CTL) increasing. Broad hepatocyte was necrosised by CTL.

The crude polysaccharide of *Antrodia camphorata* was effective in scavenging oxygen free radical formation and increasing IL-2. In this invention, it was found that both crude polysaccharide and neutral polysaccharide (ACN2a) had protective effect against *P. acnes*-LPS induced hepatic toxicity in mice. It was conceivable that the polysaccharide of *Antrodia camphorata* exerted its hepatoprotectie activity by, at least partly, scavenging oxygen free radical formation, resulting in obstructing the 2) way of *P. acnes*-LPS induced hepatic toxicity or by increasing IL-2, resulting in decreasing CTL and protecting liver.

Example 7

Extraction and Isolation of *Antrodia Camphorata*

*Antrodia camphorata* mycelia powder (ACM) (60 g), from Simpson Biotech Co. Ltd., Taiwan, October 2001, were three times extracted with $CHCl_3$ for 3 h under reflux. The $CHCl_3$ extract (5.3 g) was chromatographed on silica gel eluted with n-hexane-acetone (19:1-14:6), and $CHCl_3$-MeOH (1:1) to give nine fractions (Fr. 1-9). Fraction 2 was chromatographed on silica gel to give compound 1 (8.7 mg). Fraction 4 was chromatographed on normal and reversed phase silica gel to give compound 2 (13.6 mg). Fraction 5 was chromatographed on silica gel eluted with n-hexane-acetone (8:2) to give ergosterol peroxide (35.8 mg). Fraction 6 gave compound 3 (14.6 mg) by combination of normal and reversed phase silica gel column chromatography. Fraction 7 yielded a mixture of compounds 4 and 5 (4:1) by column chromatography. The mixture of compounds 4 and 5 were subsequently separated by preparative HPLC [column: Tosoh TSK-gel ODS-80T$_M$ (21.5×300 mm), mobile phase: $CH_3OH$—$H_2O$ containing 0.1% TFA (70:30)].

3-isobutyl-4-[4-(3-methyl-2-butenyloxy)phenyl]-1H-pyrrol-1-ol-2,5-dione (compound 3):

yellow oil; UV (MeOH) $\lambda_{max}$ (log ∈): 232.5 (4.3), 296 (3.7), 374 (3.7) nm; IR ($CHCl_3$) $v_{max}$ 1717 $cm^{-1}$; $^1$H-NMR Table 1; $^{13}$C-NMR Table 2; EIMS m/z 329 [M]$^+$ (12), 261 (100), 131 (50); HR-EIMS m/z: 329.1637 (Calcd for $C_{19}H_{23}NO_4$, 329.1627).

Example 8

Protective Effect of *Antrodia Camphorata* on Fulminant Hepatitis

One of the animal models of human viral hepatitis is *Propionibacterium acnes*-lipopolysaccharide (*P. acnes*-LPS) induced mouse hepatitis. This mouse experimental hepatitis model is widely accepted for studying fulminant hepatitis such as human viral hepatitis. This animal model has been taken to evaluate the protective efficacy of extracts of *Antrodia camphorata* and compound 3 on fulminant hepatitis. The effectiveness of the chemicals and the extracts was determined by measuring the serum concentration of glutamic oxaloactic transminase (GOT), glutamic pyruvic transaminase (GPT), total protein, and albumin in the hepatitis mice.

Methods and Equipments

Animals

ICR mice were purchased from SLC Co., Ltd. (Shizuoka, Japan). They were kept in an air-conditioned animal room and took water and feed ad libitum. Animal quarantine period was longer than one week.

*P. acnes*, ATCC 6919, was purchased from Science Research Institute in Saitama Japan. It was cultured in a medium which contains brain heart infusion, L-cystein (0.03%), Tween80 (0.03%) in distilled water under anaerobic condition at 37° C. for 48 hours. At the termination of the culture, *P. acnes* were spun down at 7000 rpm and 4° C. for 15 minutes. After spinning, the collected *P. acnes* were re-suspended with PBS and was spun down again. Then the collected *P. acnes* was suspended again with PBS. The suspension solution was heated at 80° C. for 30 minutes and freeze-dried to prepare powder.

Fractionation of Mycelium of *Antrodia Camphorata*

Thirty gram of *Antrodia camphorata* mycelia (Lot #: C071202-1) was mixed with 100 ml chloroform. The mixture was extracted by refluxing at 40° C. for 1 hour. The reflux procedure was repeated three times. All extracts were combined and prepared as freeze-dried powder. The final volume of 4.5 g of powder was obtained. The residue of chloroform extraction was refluxed with 100 ml boiling water for 1 hour. The procedure was also repeated three times. All water extract were freeze-dried.

Administration

The water extract was dissolved in distilled water. The chloroform extract and compound 3 were suspended in distilled water with 4% Tween 80.

Serum Measurement

Sera were separated by centrifugation blood at 3000 rpm, 4° C. for 15 minutes. GOT and GPT were measured by using transaminase CII-Test Wako (Wako Jyun-Yaku Co., Ltd. Osaka). Total protein and albumin were measured by using A/G B-Test Wako (Wako Jyun-Yaku Co., Ltd. Osaka).

Experiment Procedures

The mouse fulminant hepatitis was induced as follows: ICR male mice (8 weeks old) received 0.5 mg of heat-killed *Propionibacterium acnes* (*P. acnes*) by intravenous injection. On the 8th days after the *P. acnes* injection, mice were challenged with 0.25 mg of LPS by intravenous injection to induce fulminate hepatitis. Extracts of *Antrodia camphorata* and compound 3 were given to mice orally by a gastric tube once a day for eight consecutive days right after *P. acnes* injection. Thereafter, in order to assess the effect of the test substances, mice sera were collected at 18 hours after the LPS challenge.

Results

The survival rate of the control group (mice administered with water) was 30%. Mice that received water extract of *Antrodia camphoarata* at doses of 200 mg/kg and 50 mg/kg showed survival rates of 60% and 40%, respectively.

The average GOT titer of the control mice was 1662 IU/L, and the average GOT titers of mice treated with 200 mg/kg, and 50 mg/kg water extract were 208 IU/L and 1159 IU/L, respectively. The average GPT titers of the control mice, mice treated with 200 mg/kg and 50 mg/kg water extract of *Antrodia camphoarata* were 1256 IU/L, 193 IU/L, and 697 IU/L, respectively.

The concentration of total protein and albumin in fulminate hepatitis mice was also reduced in mice treated with water extract of *Antrodia camphoarata* compared to the control mice. The concentration of total protein of mice treated with 200 mg/kg water extract of *Antrodia camphoarata* the total protein concentration recovered to the normal level, but not the concentration of albumin.

Figure 14:
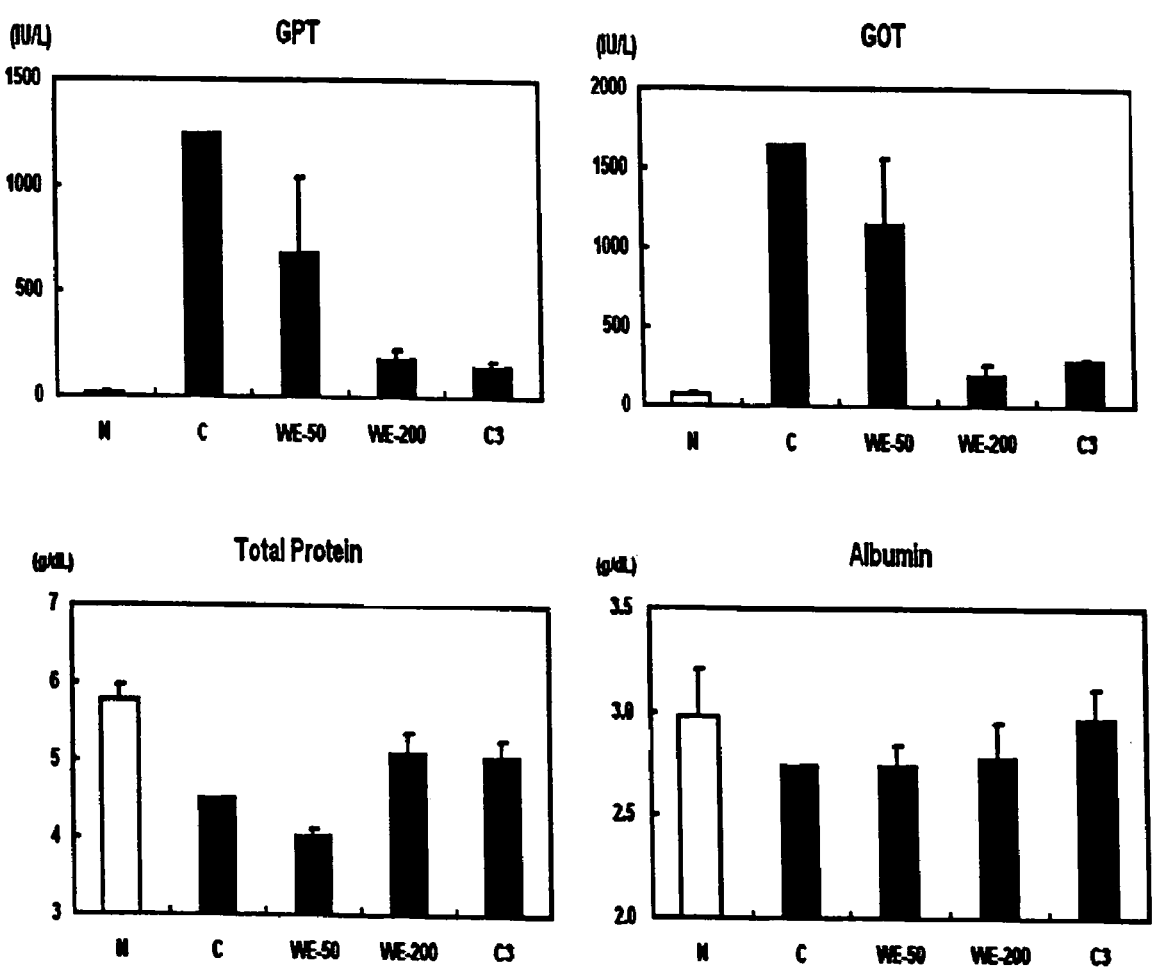
FIG. 14 illustrates serum constituents in mice with *P. acnes* plus LPS-induced liver injury. In the Figure, N means normal group, C means control group, WE-50 means water extract (50 mg/kg), WE-200 means water extract (200 mg/kg) and C3 means compound 3 of the invention (20 mg/kg).
Figure 15:
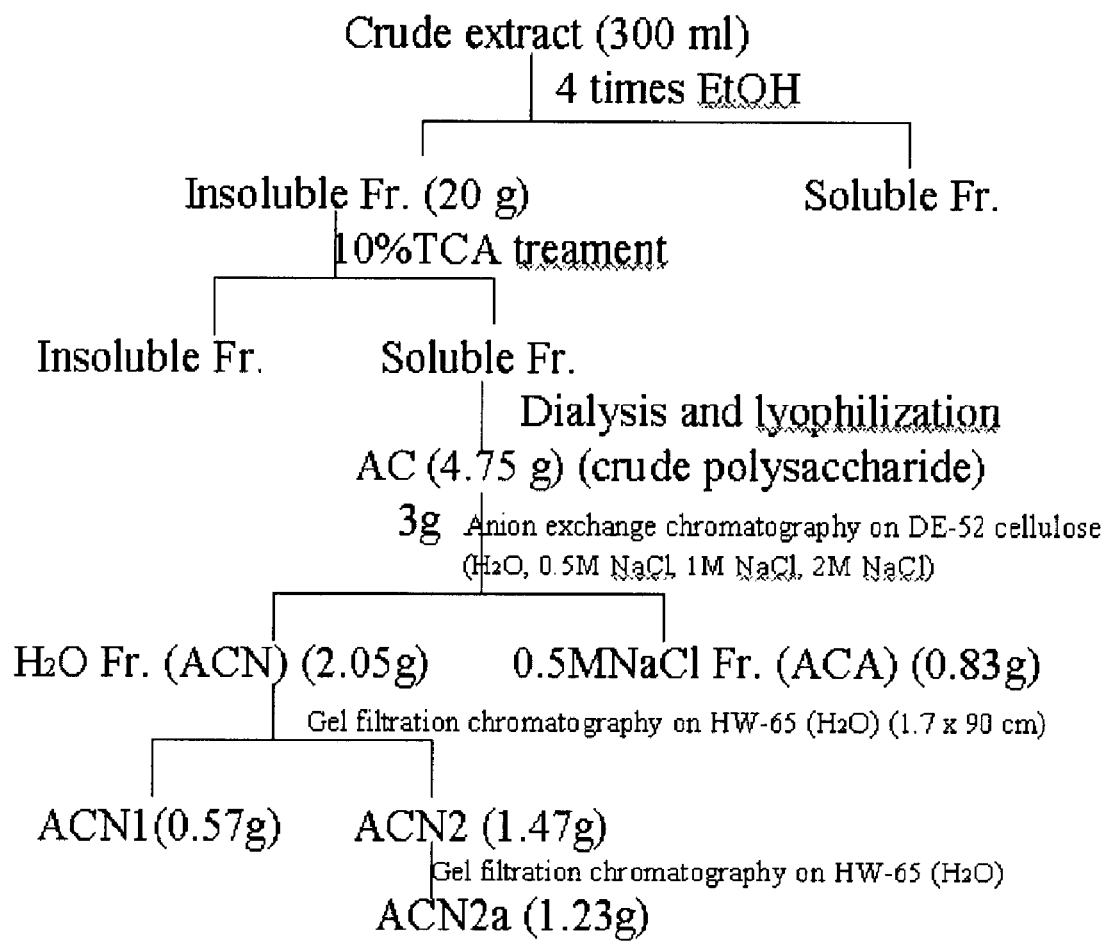
FIG. 15 illustrates the fractionation of the hot water extract of the *Antrodia camphorate*.
Figure 16:
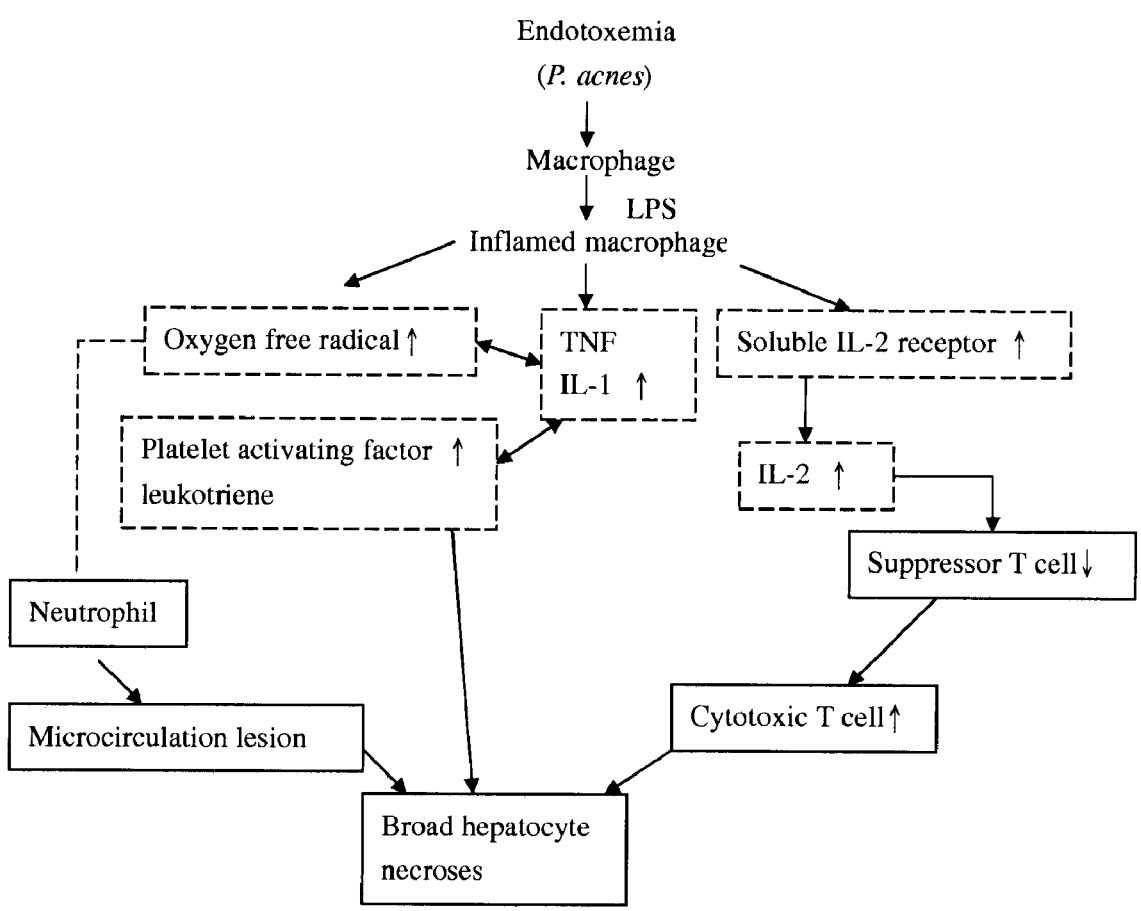
FIG. 16 illustrates the mechanism of *P. acnes*-LPS induced hepatic toxicity.

These experimental results (FIG. 14) suggested that water extract of mycelium of *Antrodia camphorata* from *Antradia camphoarata*, have a potent hepato-protective effect against fulminant hepatitis.

What is claimed is:

1. A polysaceharide extracted from *Antrodia camphorata* by (1) using $CHCl_3$ to extract freeze-dried power of *Antrodia Camphorata*, (2) dipping the residue into 100° C. water to extract, (3) adding EtOH to the extract, (4) stirring the mixture and put it into a refrigerator for one night, (5) filtering and washing precipitate with cold EtOH, (6) treating precipitate with 10% trichloroacetic acid (TCA), (7) dialyzing the TCA-soluble fraction obtained by centrifugation against distilled water, and (8) lyophilizing the nondialyzed portion, wherein the polysaccharide has characteristics as follows:
   (a) appearance: colorless and shapeless powder,
   (b) pH: neutral,
   (c) molecular weight: 1285 kDa determined by HPLC as shown in FIG. 4,
   (d) rotatory power: $[\alpha]_D$+115.0° (c=0.4433, $H_2O$),
   (e) intrinsic viscosity: $[\eta]$=0.0417 dl·g$^{-1}$,
   (f) specific heat Cp: 0.2663 Cal/g·° C.,
   (g) IR spectrum: as shown in FIG. 5,
   (h) $^1$H-NMR spectrum: as shown in FIG. 6,
   (i) $^{13}$C-NMR spectrum: as shown in FIG. 7, and
   (j) GC-MS analysis: as shown in FIG. 8.

2. The polysaccharide as claimed in claim 1, wherein the IR spectrum of the polysaccharide shows that the component sugars of the polysaccharide comprises galactose, glucose, fucose, mannose and galactosamine.

3. The polysaccharide as claimed in claim 2, wherein the $^1$H-NMR spectrum of the polysaccharide further shows that the component sugars of the polysaccharide comprises D-galactose, D-glucose, L-fucose and D-mannose.

4. The polysaceharide as claimed in claim 3, wherein the ratio of the component sugars comprising galactose, glucose, fucose, mannose and galactosamine is 1:0.24:0.07:0.026:faint.

5. The polysaccharide as claimed in claim 4, wherein the component sugars have a main chain consisting of:
   (a) a terminal residue comprising fucose or glucose, and
   (b) a middle residue selected from the group consisting of 1,3-linked glucose, 1,4-linked glucose, 1,6-linked and 1,2,6-linked galactose, and wherein the 1,2,6-linked galactose residue is attached by a branch chain at a 2-O site.

6. The polysaccharide as claimed in claim 5, wherein the polysaccharide includes a main backbone comprising a galactose residue.

7. The polysaccharide as claimed in claim 1, wherein the polysaccharide is extracted from at least one of mycelium or fruit body of *Antrodia camphorate*.

8. A method for extracting the polysaccharide of claim 1, the method comprises:
   (a) extracting the *Antrodia camphorata* by water,
   (b) collecting the precipitates of the mixture, and
   (c) dialyzing the TCA-soluble fraction.

9. The method as claimed in claim 8, wherein the step (a) is around 60-120° C.

10. The method as claimed in claim 8, wherein the step (b) is left the mixture around 0-20° C.

11. The method as claimed in claim 8, wherein the precipitates are treated with trichloroacetic acid (TCA).

12. A composition for providing hepatoprotective effects to a subject in need thereof, the composition comprises a polysaccharide from *Antrodia camphorata* as claimed in claim 1.

13. The composition as claimed in claim 12, wherein the hepatoprotective effect is inhibiting or reducing necrosis in a hepatocyte.

14. The composition as claimed in claim 13, wherein the necrosis is reduced via scavenging oxygen free radical formation, increasing IL-2, or decreasing cytotoxic T lymphocyte.

15. The composition as claimed in claim 12, wherein the hepatoprotective effect is against fulminant hepatitis.

16. A method for providing a hepatoprotective effect to a patient in need thereof, the method comprises administering to the patient an effective amount of a polysaccharide extract from *Antrodia camphorata* as claimed in claim 1, and wherein the hepatoprotective effect is against fulminant hepatitis.

* * * * *